United States Patent [19]

Mills

[11] Patent Number: 5,710,002
[45] Date of Patent: Jan. 20, 1998

[54] **DETECTION OF *CLAVIBACTER MICHIGANENSIS* SUBSP. SEPEDONICUS**

[75] Inventor: Dallice L Mills, Corvallis, Oreg.

[73] Assignee: Oregon State University, Corvallis, Oreg.

[21] Appl. No.: 488,144

[22] Filed: Jun. 7, 1995

[51] Int. Cl.$^6$ ............... C12Q 1/68; C12P 19/34; C07H 21/04

[52] U.S. Cl. ............ 435/6; 435/91.2; 435/252.3; 435/320.1; 536/23.7; 536/24.32; 536/24.33; 536/25.4; 935/8; 935/9; 935/22; 935/66; 935/78

[58] Field of Search .............. 435/6, 91.2, 252.3, 435/320.1, 172.3; 536/24.32, 24.33, 23.7, 25.4; 935/8, 9, 22, 66, 77, 78

[56] References Cited

U.S. PATENT DOCUMENTS 4,683,202  7/1987  Mullis ............................... 435/91

FOREIGN PATENT DOCUMENTS 8803957  6/1988  WIPO.
WO93/03187  7/1992  WIPO.

OTHER PUBLICATIONS

Schneider et al, FEMS Microbiology Letters (1993) 109: 207–212.

Mirza et al, Canadian Journal of Microbiology (1993) 39:1029–1034.

Rademaker et al. Canadian Journal of Microbiology (1994) 40: 1007–1018.

Drennan et al., "Comparison of a DNA Hybridization Probe and ELISA for the Detection of *Clavibacter michiganensis* subsp. sepedonicus in Field–Grown Potatoes." *Plant Dis.*, 77:1243–1247 (1993).

Mogen et al., "Homology of pCS1 Plasmid Sequences with Chromosomal DNA in *Clavibacter michiganese* subsp. sepedonicum: Evidence for the Presence of a Repeated Sequence and Plasmid Integration." *Appl. Environ. Microbiol.*, 53:2476–2481 (1987).

Mogen et al., "Distribution and Partial Characterization of pCS1, a Highly Conserved Plasmid Present in *Clavibacter michiganese* subsp. sepedonicum." *Phytopathology*, 78:1381–1386 (1988).

Dopfer et al., "Nucleic Acid Hybridization Studies on Microbacterium Curtobacterium, Agromyces and Related Taxa," *J. Gen. Microbiol.*, 128:1697–1708 (1982).

Williams et al., "Development of a DNA Probe for the Detection of *Corynebacterium Sepedonicum*," *Phytopathology*, 82:1145 (1992) (Abstract A773).

Firrao et al., "Identification of *Clavibacter michiganensis* subsp. sepedonicus Using the Polymerase Chain Reaction," *Can. J. Microbiol.*, 40:148–151 (1994).

Wieland et al., "A Method for Difference Cloning: Gene Amplification Following Subtractive Hybridization," *Proc. Natl. Acad. Sci. USA*, 87:2720–2724 (1990).

Kunkel et al., "Specific Cloning of DNA Fragments Absent from the DNA of a Male Patient with an X Chromosome Deletion," *Proc. Natl. Acad. Sci. USA*, 82:4778–4782 (1985).

Darrasse et al., "Isolation by Genomic Subtraction of DNA Probes Specific for *Erwinia carotovora* subsp. atroseptica," *Appl. Environ. Microbiol.*, 60:298–306 (1994).

Straus et al., "Genomic Subtraction for Cloning DNA Corresponding to Deletion Mutations," *Proc. Natl. Acad. Sci. USA*, 87:1889–1893 (1990).

*Primary Examiner*—Carla J. Myers
*Attorney, Agent, or Firm*—Klarkquist Sparkman Campbell Leigh and Whinston, LLP

[57] ABSTRACT

The present invention provides genomic DNA sequences unique to *Clavibacter michiganensis* ssp. sepedonicus (Cms) that are useful as probes and primers for the detection of the presence of Cms nucleic acids in a biological sample, e.g., by means of the polymerase chain reaction.

23 Claims, 1 Drawing Sheet

DETECTION OF *CLAVIBACTER MICHIGANENSIS* SUBSP. SEPEDONICUS

ACKNOWLEDGMENT OF GOVERNMENT SUPPORT

This invention was made with government support under Grants Nos. SCA 58-3K47-9-023 and 58-1275-4-022, awarded by the United States Department of Agriculture (USDA) Agricultural Research Service. The government has certain rights in this invention.

BACKGROUND

This invention is related to the field of detection of plant pathogens, particularly to the detection of the causative agent of bacterial ring rot disease of potato, *Clavibacter michiganensis* ssp. sepedonicus.

Bacterial ring rot disease of potato (BRR) is caused by a Gram positive bacterium, *Clavibacter michiganensis* subspecies (ssp.) sepedonicus (Cms) (Spieck. and Kotth.) Skapat. and Burkh. BRR is a major concern of seed potato producers in the U.S. as well as those countries that import U.S. seed and tablestock potatoes. The presence of this bacterium in seed stock can result in the loss of an entire seed lot.

BRR has been recorded in all potato-growing areas of the U.S., in the Scandinavian countries including Finland, and in Germany. It has either been eradicated or was never present in most other European countries. Among the various potato diseases, only BRR has been assigned a zero tolerance rating. The European Economic Community (EEC) excludes shipments of seed potatoes that originate in areas where the disease is present.

Because of the widespread occurrence of BRR in the U.S., the market for potatoes exported from the U.S. is severely limited. Although the total annual production of potatoes by the U.S. is estimated at approximately 1.75 million metric tons, only about 0.2% of this crop is exported to Canada and only 0.05% is exported to all other countries. The major exporters of seed potatoes are members of the EEC.

There is general acceptance among scientists throughout the world that more sensitive and confirmatory tests are needed for the detection of Cms, especially in symptomless plants and tubers. Diagnosis of BRR in seed lots is largely dependent upon the occurrence of disease symptoms (Manzer and Kurowski, Am. Potato J. 69:363, 1992), but some infected plants are asymptomatic. Current methods of detection of this pathogen in seed rely upon immunofluorescence procedures (De Boer et al., Plant Dis. 72:874, 1988), Gram staining (De Boer and Slack, Plant Dis. 68:841–844, 1984) and a bioassay on an alternate host, eggplant (discussed in Drennan et al., Plant Dis. 77:1243–1247, 1993). Detection by immunofluorescence is very sensitive, but positive identification is sometimes compromised by low populations and occasional cross reactivity with other microbes. The eggplant bioassay is protracted and costly, necessitating large growth room facilities to screen numerous samples.

A recent alternative approach for the detection of Cms was the development of a DNA probe from a 1.078 kb repeated sequence (Drennan et al., Plant Dis. 77:1243–1247, 1993) that was cloned from an indigenous, integrative plasmid, pCS1 (Mogen and Oleson, Appl. Environ. Microbiol. 53:2476–2481, 1987; Phytopathology 78:1381–1386, 1988). The repeat is also found within the bacterial chromosome of Cms strains. Unfortunately, probes made from this repeated sequence are not specific for Cms strains; they hybridize not only with Cms strains from diverse geographic locations but also with sequences in the genome of several strains of *C.m. insidiosum.*

Presently, there is no method of detection of Cms that is both sensitive and unfailingly specific. No Cms-specific DNA fragments have been described in the literature. A highly sensitive and specific means for detection of Cms would be extremely desirable to limit potato crop losses to bacterial ring rot and to ensure the U.S. an enhanced opportunity in worldwide seed potato export markets. The present invention meets these and other needs.

SUMMARY OF THE INVENTION

The present invention provides isolated nucleic acids comprising a nucleotide sequence unique to *Clavibacter michiganensis* ssp. sepedonicus (Cms), preferably unique to the Cms chromosome. Such isolated nucleic acids may be produced by subtractive hybridization as described in greater detail below. Preferably, the isolated nucleic acids of the invention comprise at least 15 contiguous nucleotides of a unique Cms nucleotide sequence or a nucleotide sequence complementary thereto. The nucleic acids of the present invention may further comprise a detectable label, preferably a nonradioactive label. Also provided by the present invention is a recombinant vector comprising such an isolated nucleic acid and a transformed host cell comprising such a vector.

The present invention also provides methods for detecting the presence of a Cms cell in a biological sample comprising the steps of: (1) providing the biological sample; (2) contacting the biological sample with at least one isolated nucleic acid comprising a nucleotide sequence unique to Cms under conditions conducive to hybridization of the isolated nucleic acid to a complementary DNA molecule, thereby forming a hybrid nucleic acid; and (3) detecting the hybrid nucleic acid. Preferably, the isolated nucleic acid further comprises a label and the step of detecting the hybrid nucleic acid comprises detecting the presence of the label. Such a detection method preferably employs a pair of primers, each primer comprising an isolated nucleotide sequence unique to Cms. Such primers may be used to perform a DNA amplification reaction, e.g., the polymerase chain reaction (PCR), thereby producing an amplification product; detecting the presence of the amplification product indicates the presence of Cms in the sample.

In another embodiment, the present invention provides a method of isolating a nucleic acid sequence unique to *Clavibacter michiganensis* ssp. sepedonicus comprising the steps of: providing *Clavibacter michiganensis* ssp. sepedonicus tester DNA; providing driver DNA comprising DNA from a bacterial species related to Cms; hybridizing the tester DNA to the driver DNA; isolating tester DNA that does not hybridize to the driver DNA, thereby producing unique tester DNA comprising a nucleic acid sequence unique to *Clavibacter michiganensis* ssp. sepedonicus; and isolating the nucleic acid sequence unique to *Clavibacter michiganensis* ssp. sepedonicus. The present invention also provides isolated nucleic acid sequences unique to *Clavibacter michiganensis* ssp. sepedonicus produced by such a method.

BRIEF DESCRIPTION OF THE DRAWING

FIG. 1 is a flow chart outlining the various steps comprising a subtractive hybridization method by which Cms DNA was enriched for Cms-specific DNA fragments.

DETAILED DESCRIPTION OF THE INVENTION

Figure 1:
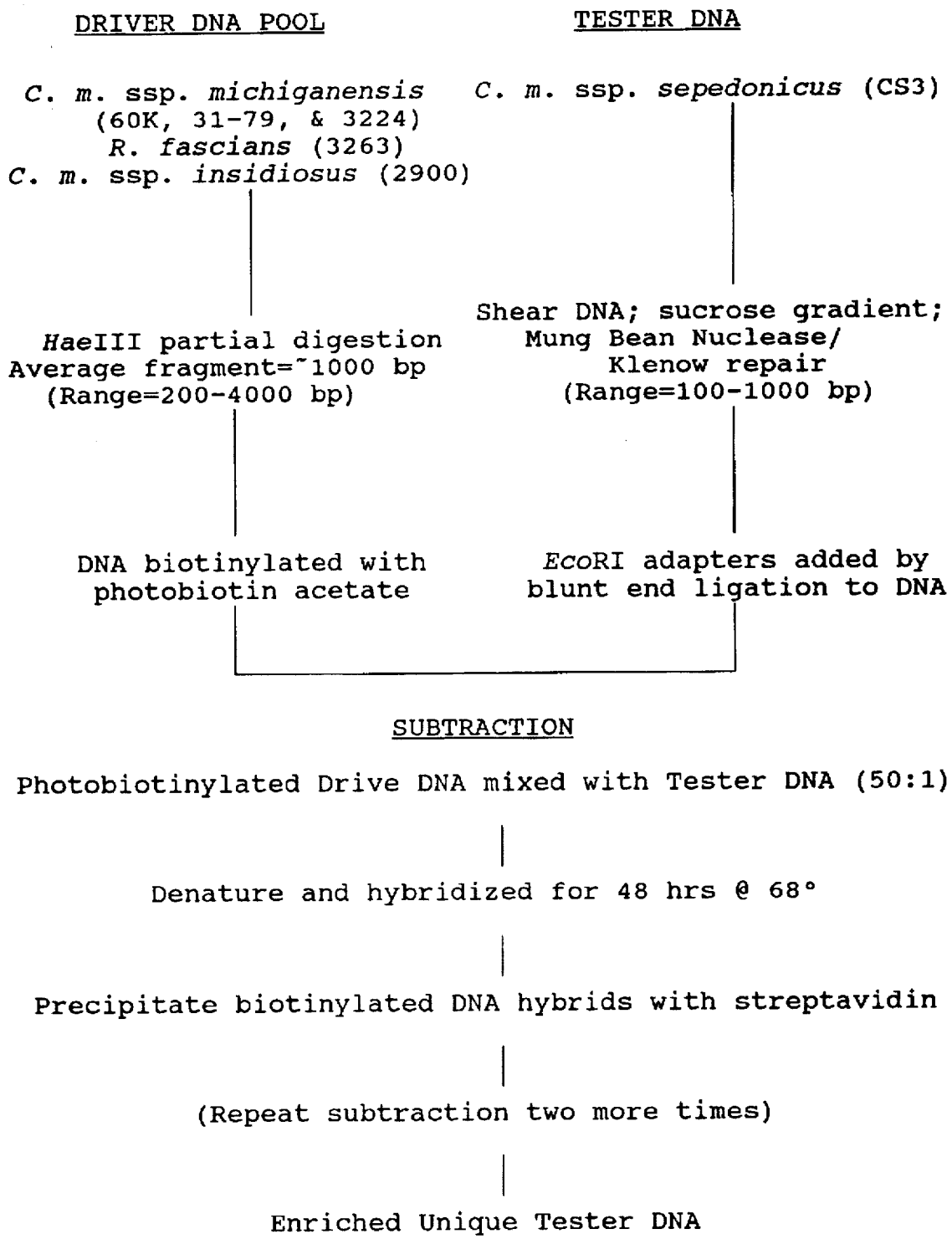

The present invention provides compositions and methods for detecting Cms in a biological sample. Genomic DNA sequences unique to Cms have been isolated by subtractive hybridization. These sequences are useful as probes and primers for the highly sensitive detection of the presence of Cms nucleic acids in a biological sample.

In a preferred embodiment of the invention, pairs of primers complementary to opposite strands of one or more of these unique DNA sequences, e.g., complementary to internal regions near the termini of each sequence, are contacted with a biological sample under conditions conducive to nucleic acid hybridization and amplification, e.g., by the polymerase chain reaction (PCR). The presence of Cms in the sample is demonstrated by detection of an amplification product. Amplification primers based on the nucleotide sequence of the unique Cms genomic sequences are both extremely specific and highly sensitive. Cms nucleic acids present in a small number of cells can be amplified into millions of copies within hours, thereby allowing detection of the organism in potato seed stock from asymptomatic plants.

The value of the detection compositions and methods of the present invention depends entirely upon the identification of DNA sequences that are truly unique to Cms strains, i.e., that hybridize to Cms DNA under conditions described below, but do not hybridize to DNA from closely related bacterial species. DNA hybridization studies have suggested that approximately 25% of the genome of C. m. ssp. sepedonicus contains sequences not present in other closely related bacteria (Dopfer et al., J. Gen. Microbiol. 128:1697–1708, 1982).

DNA clones unique to the genome of Cms were obtained by a procedure called subtractive hybridization, as outlined in FIG. 1. C. m. ssp. sepedonicus (CS3) "tester DNA" was prepared by randomly shearing C. m. ssp. sepedonicus (CS3) DNA and subjecting the sheared DNA to sucrose gradient centrifugation in order to obtain fragments in the size range of 100 to 1000 base pairs (bp). The ends of these fragments were repaired by the use of mung bean nuclease and the Klenow fragment of DNA polymerase I. EcoRI adapters were then added to the Cms fragments by blunt end ligation. "Driver DNA" was also prepared from DNA pooled from several bacterial species related to Cms (C. m. ssp. michiganensis strains 60K, 31–79 and 3224, *Rhodococcus facians* strain 3263 and C. m. ssp. insidiosus strain 2900) which had been subjected to partial digestion with HaeIII to generate fragments with an average size of approximately 1000 bp then biotinylated with photobiotin acetate. The tester DNA was hybridized to a 50-fold excess of driver DNA and biotinylated DNA, including tester:driver DNA hybrids, were "subtracted" out with streptavidin. After several rounds of subtraction, the DNA which remained was enriched for sequences unique to C. m. ssp. sepedonicus (CS3).

This enriched tester DNA ("unique tester DNA") was subsequently amplified by the polymerase chain reaction (PCR) and cloned. The cloned unique tester DNA was then screened for specific homology to C. m. ssp. sepedonicus by hybridization to slot blots containing total DNA from numerous strains of related and unrelated species. Several clones hybridized only to C. m. ssp. sepedonicus (CS3) and thus would be useful in preparing highly specific nucleic acid probes or primers for detecting Cms in a sample. Additional unique Cms sequences may be obtained by repeating this genomic subtraction procedure and screening the clones for unique Cms sequences as described in detail below. Such additional sequences are also considered to be included among the nucleic acids of the present invention.

Additional unique Cms sequences are obtained, for example, by obtaining sequences flanking unique Cms sequences obtained through genomic subtraction. For example, one may use all or a portion of a unique Cms sequence provided below as a probe to obtain such sequences from total genomic DNA or from a genomic library by hybridization.

Alternatively, such flanking sequences may be obtained, for example, by amplification (e.g., PCR) using a first primer having a sequence based on a unique Cms sequence provided below, preferably based on an end of such a sequence. Where the genomic DNA comprises DNA fragments having known adaptor or vector sequences at the fragment ends, a second primer can be used that hybridizes to the adaptor or vector. Where the genomic DNA lacks such adaptor or vector sequences within several kilobase pairs of the site to which the first primer hybridizes, a random sequence primer may be used, and amplification products of the desired size selected by standard means (e.g., by agarose gel electrophoresis followed by isolation of amplified DNA of the desired size range from the gel).

A pair of primers based on a single unique Cms sequence is sufficiently sensitive and specific for detection of Cms in a biological sample. Specificity may be further improved by using multiple primer pairs, each pair derived from different regions of a single unique sequence or from different unique sequences, e.g., one pair derived from Cms 72 and another pair derived from Cms 85. In this way one can corroborate a positive result obtained from the use of a single primer pair.

DEFINITIONS AND METHODS

The following definitions and methods are provided to better define the present invention and to guide those of ordinary skill in the art in the practice of the present invention. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994.

Nucleic acids

Nucleic acids useful in the practice of the present invention comprise isolated nucleic acids unique to Cms, preferably to the chromosome of Cms. Preferably these sequences are separated by several kilobases on the chromosome of Cms. Also included are nucleic acids that are "substantially similar" to such naturally occurring nucleic acids, as defined below.

The nucleic acids of the present invention may be free or bound to a solid support, such as a hybridization membrane (e.g., nitrocellulose or nylon), a bead, or other solid supports known in the art.

"Isolated". An "isolated" nucleic acid has been substantially separated or purified away from other nucleic acid sequences in the cell of the organism from which it naturally occurs, i.e., other chromosomal and extrachromosomal DNA and RNA. Thus, the claimed nucleic acids would not embrace entire naturally occurring bacterial chromosomes. The term "isolated" thus encompasses nucleic acids purified by standard nucleic acid purification means. It also embraces nucleic acids prepared by recombinant expression in a host cell and chemically synthesized nucleic acids.

The nucleic acids of the present invention comprise at least the minimum length able to hybridize specifically with nucleic acids of Cms (or a sequence complementary thereto) under stringent conditions. The length of a nucleic acid of the present invention is preferably 15 nucleotides or more, although a shorter nucleic acid may be employed as a probe or primer if shown empirically to specifically hybridize under stringent conditions with nucleic acids of Cms by methods well known in the art.

Probes and primers. Nucleic acid probes and primers may readily be prepared based on the isolated Cms-specific nucleic acids provided by the present invention. A probe comprises an isolated nucleic acid attached to a detectable label or reporter molecule well known in the art. Typical labels include radioactive isotopes, ligands or antiligands, chemiluminescent agents, and enzymes. Methods for labeling and guidance in the choice of labels appropriate for various purposes are discussed, e.g., in *Molecular Cloning: A Laboratory Manual*, 2nd ed., vol. 1–3, ed. Sambrook et al., Cold Spring Harbor Laboratory Press: Cold Spring Harbor, N.Y., 1989; and *Current Protocols in Molecular Biology*, ed. F. Ausubel et al., Greene Publishing and Wiley-Interscience: New York, 1987 (with periodic updates). Non-radioactive labels are preferred to facilitate the use of the probes and primers of the invention in the field.

Primers are short nucleic acids, generally DNA oligonucleotides 15 nucleotides or more in length, which are annealed to a complementary target DNA strand by nucleic acid hybridization to form a hybrid between the primer and the target DNA strand and extended along the target DNA strand by a polymerase, preferably a DNA polymerase. Primer pairs may be used for amplification of a nucleic acid sequence, e.g., by the polymerase chain reaction (PCR) or other nucleic acid amplification methods well known in the art.

Probes and primers, including primer pairs for various nucleic acid amplification techniques, may be prepared and used by any of the methods known in the art. Such methods are described, for example, in Sambrook et al. (1989), Ausubel et al. (1987), and Innis et al., *PCR Protocols: A Guide to Methods and Applications*, Academic Press: San Diego (1990). PCR primer pairs may be derived from the unique Cms sequences, for example, by using computer programs intended for that purpose such as Primer (Version 0.5, © 1991, Whitehead Institute for Biomedical Research, Cambridge, Mass.).

To assist in the preparation of probes and primers, the nucleotide sequence of a number of DNA molecules unique to Cms have been provided. These sequences may be confirmed by using PCR or other amplification methods to amplify Cms genomic DNA using primers fashioned on the basis of the nucleotide sequences presented herein, then sequencing the amplification product. It is preferred that such probes and primers are substantially similar, and most preferably are identical, to the unique Cms sequences presented herein or obtained by means of the subtractive hybridization protocol described below. The nucleotide sequence of any such unique Cms DNA may readily be determined by methods well known in the art.

"Amplified DNA"; methods for nucleic acid amplification. As used herein, "amplified DNA" refers to the product of nucleic acid amplification of a target nucleic acid sequence.

A number of different nucleic acid amplification methods are known in the art, including the polymerase chain reaction (PCR). A variety of PCR methods are described, inter alia, in U.S. Pat. Nos. 4,683,195 and 4,683,202 and in *PCR Protocols: A Guide to Methods and Applications*, Innis et al. eds., Academic Press, San Diego, 1990. Reagents and apparatus for performing PCR are commercially available, e.g., from Perkin-Elmer/Cetus Instruments (PECI) of Norwalk, Conn.

Briefly stated, PCR is a cyclical process for the amplification of a nucleic acid template comprising the steps of: (a) denaturation of the template (generally by heating to 95° C. to 100° C.), (b) hybridization of dual oligodeoxynucleotide primers to the denatured template, and (c) template replication, consisting of an extension of these primers by a DNA polymerase (generally a thermostable polymerase such as Taq polymerase). Among the other reagents necessary for PCR are deoxynucleotide triphosphates (dNTPs, i.e., A, C, G, and T and their analogues) and a buffer to provide, for example, the salt and pH conditions necessary for optimal polymerase activity.

The primers are so designed that they hybridize to sequences flanking the region to be amplified, one on each strand, and that the single strand generated by extension of each primer can act as a template for the extension of the other primer. Thus, each cycle of replication provides a two-fold amplification of the template. PCR can thus be used to amplify target DNA sequences several million-fold, allowing the product of the amplification of a single target nucleic acid sequence to be detected and analyzed by well known means.

For the practice of the present invention, oligonucleotides primers for nucleic acid amplification ("amplification primers") preferably hybridize specifically to a particular nucleotide sequence ("target sequence") in the chromosome of Cms ("target chromosome").

A number of suitable commercially available DNA polymerases are appropriate for performing PCR. Thermostable polymerases are preferred, such as those obtained from *Thermus aquaticus* (Taq polymerase) or *T. flavis*. For PCR or other amplification procedures, or for DNA sequencing reactions, other polymerases may be appropriate, including *E. coli* DNA polymerase I or its Klenow fragment, reverse transcriptase, phage T4 or T7 polymerases, or structural variants and modified forms of these and other polymerases.

For performing the amplification reaction, a buffer solution is used that provides a pH and salts or other compounds suitable for optimal activity of the DNA polymerase. A typical PCR buffer contains 10 to 50 mM Tris-HCl (between pH 8.3 and 8.8) when measured at 20° C., 50 mM KCl and 1.5 mM $MgCl_2$.

To detect PCR-amplified products, a sample may, for example, be electrophoresed on an agarose or polyacrylamide gel. Smaller DNA fragments resulting from amplification are preferably analyzed by polyacrylamide gel electrophoresis. DNA bands are visualized by ethidium bromide staining, or, to increase sensitivity, gel electrophoresis can be followed by Southern blotting or dot blotting and hybridization with a labeled probe by techniques well known in the art. Also, a detectable label may be incorporated into the amplified DNA product to assist in visualization of the amplification product and thus increase sensitivity.

Substantial similarity. A first nucleic acid is "substantially similar" to a second nucleic acid if, when optimally aligned (with appropriate nucleotide insertions or deletions) with the other nucleic acid (or its complementary strand), there is nucleotide sequence identity in at least about 75–90% of the nucleotide bases, and preferably greater than 90% of the nucleotide bases. ("Substantial sequence complementarity" requires a similar degree of sequence complementarity.) Sequence similarity may be determined by comparing the nucleotide sequences of two nucleic acids using sequence analysis software such as the Sequence Analysis Software Package of the Genetics Computer Group, University of Wisconsin Biotechnology Center, Madison, Wis.).

Nucleic acid hybridization; "Stringent conditions"

The nucleic acid probes and primers of the present invention hybridize under stringent conditions to total DNA, and preferably to the chromosome, of Cms.

The term "stringent conditions" is functionally defined with regard to the hybridization of a nucleic acid probe to a target nucleic acid (i.e., to a particular nucleic acid sequence of interest) by the hybridization procedure discussed in Sambrook et al., 1989 at 9.52–9.55. See also, Sambrook et al., 1989 at 9.47–9.52, 9.56–9.58; Kanehisa, Nuc. Acids Res. 12:203–213, 1984; and Wetmur and Davidson, J. Mol. Biol. 31:349–370, 1968. Regarding the amplification of a target nucleic acid sequence (e.g., by PCR) using a particular amplification primer pair, stringent conditions are conditions that permit the primer pair to hybridize only to the target nucleic acid sequence to which a primer having the corresponding wild-type sequence (or its complement) would bind. Where the target nucleic acid sequence is present at only one copy in a genome, for example, amplification of the genomic DNA under stringent conditions will produce a single amplification product.

Nucleic acid hybridization is affected by such conditions as salt concentration, temperature, or organic solvents, in addition to the base composition, length of the complementary strands, and the number of nucleotide base mismatches between the hybridizing nucleic acids, as will be readily appreciated by those skilled in the art.

Operably linked. A first nucleic acid sequence is operably linked with a second nucleic acid sequence when the first nucleic acid sequence is placed in a functional relationship with the nucleic acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Techniques for nucleic acid manipulation are described generally in, for example, Sambrook et al., 1989; and Ausubel et al., 1987 (with periodic updates).

Preparation of recombinant or chemically synthesized nucleic acids; vectors, transformation, host cells. Large amounts of a nucleic acid of the present invention may be produced by recombinant means well known in the art or by chemical synthesis.

Natural or synthetic nucleic acids comprising a nucleotide sequence unique to the Cms genome may be incorporated into recombinant nucleic acid constructs, typically DNA constructs, capable of introduction into and replication in a host cell. Usually the DNA constructs will be suitable for replication in a unicellular host, such bacteria, but may also be intended for introduction into yeast, mammalian, plant or other eukaryotic cells.

Preferably, such a nucleic acid construct is a vector comprising a replication system recognized by the host. Vectors typically comprise, as required, an origin of replication or autonomously replicating sequence (ARS), a cloning site, preferably a unique restriction site and more preferably a polylinker sequence, and one or more selectable markers, i.e., genes encoding resistance to antibiotics or other toxic substances, complementing auxotrophic deficiencies, or supplying critical nutrients not available from complex media). Such vectors may optionally comprise expression control sequences, a promoter, an enhancer and any necessary processing information sites, including ribosome-binding sites, RNA splice sites, polyadenylation sites, transcriptional terminator sequences, mRNA stabilizing sequences, and secretion signals. In addition, the construct may be joined to an amplifiable gene (e.g., DHFR for use in mammalian host cells) so that multiple copies of the gene may be made. Promoters useful in prokaryotic, yeast, mammalian, plant, insect, and other eukaryotic hosts may include any of those well known in the art.

Examples of functional combinations of host cell lines and vectors are described in Sambrook et al., 1989, or Ausubel et al., 1987. A vector may be introduced into a host cell by various means known in the art, which vary depending on the type of cellular host, and include, but are not limited to: electroporation; transfection employing calcium chloride, rubidium chloride calcium phosphate, DEAE-dextran, or other substances; microprojectile bombardment; lipofection; and infection (where the vector is an infectious agent, such as a retroviral genome). See generally, Sambrook et al., 1989, and Ausubel et al., 1987. A cell into which has been introduced a foreign nucleic acid, such as a recombinant vector, is considered "transformed."

Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids may be performed, for example, on commercial automated oligonucleotide synthesizers.

The invention will be better understood by reference to the following examples, which are intended to merely illustrate the best mode now known for practicing the invention. The scope of the invention is not to be considered limited thereto, however.

EXAMPLES

Example 1

Use of Subtraction Hybridization to Obtain DNA Sequences Unique to C. m. ssp. sepedonicus Bacterial strains, plasmids and growth media. All strains were grown on NBY medium (Vidaver, Appl. Microbiol. 15:1523–1524, 1967) at ambient temperature. *Escherichia coli* strains DH5α (Bethesda Research Labs, Gaithersburg, Md.) and INVαF' (Invitrogen, San Diego, Calif.) were grown on Luria-Bertani (LB) medium and used for maintenance of plasmids and the clone library. Cloning was achieved using pUC vectors (Yannisch-Perron, et al., Gene 33:103–119, 1985) and the AT cloning vector, pCR1000 (Invitrogen, San Diego, Calif.).

Preparation of target and driver DNA. Total genomic DNA was extracted from all strains using the CTAB procedure (Ausubel et al., ed., Current Protocols in Molecular Biology, Green Publishing and Wiley-Interscience: New York, 1992). Target DNA was extracted from a 100 ml stationary phase culture of *C. michiganensis* ssp. sepedonicus strain Cs3, a virulent prototype strain from which the anti-C. m. ssp. sepedonicus antisera was developed for detection of this pathogen (De Boer and Wieczorek, Phytopathology 74:1431–1534, 1984; De Boer et al., Plant Dis.

72:874–878, 1988). The target DNA was treated with RNase A (100 µg/ml) (CalBiochem, La Jolla, Calif.) and concentrated by precipitation with two volumes of 95 percent ethanol. Approximately 70 µg DNA was dissolved in 1 ml of TE buffer (Sambrook et al., 1989), frozen at −70° C., and twice passed through an Eaton Pressure Cell using a Wabash Hydraulic Press, Model 12-10S (Wabash, Wabash, Ind.). An estimate of the amount of shearing was obtained by gel electrophoresis.

Approximately 20 µg of sheared DNA was centrifuged through a 14 ml gradient of 5 to 10 percent sucrose in 20 mM Tris-Cl (pH 7.0), 10 mM EDTA in a Beckman SW40 rotor at 15° C. at 85,000×g. One ml fractions were collected from each centrifuge tube and a 2 µl aliquot from each fraction was electrophoresed through a 1 percent agarose gel in order to identify fractions which contained DNA with a mean size of approximately 500 base pairs (bp). The fractions containing DNA of the appropriate size were pooled then precipitated by addition of two volumes of ethanol at −20° C.

The ends of the DNA fragments were made blunt by treatment with mung bean exonuclease III and Klenow fragment according to instructions provided by the supplier (Bethesda Research Labs, Gaithersburg, Md.). An EcoRI adaptor (SEQ ID NO: 1, nucleotides 1–16 SEQ ID NO.1 nucleotides 231–242):

```
5'-AATTCCGTTGCTGTCG
   GGCAACGACAGC
``` was then ligated to the ends of the repaired fragments according to instructions provided by the supplier (Promega Biotec, Madison, Wis.).

Driver DNA was isolated from C. m. ssp. michiganensis strains 60K, 31–79 and 3224, Rhodococcus facians strain 3263 and C. m. ssp. insidiosus strain 2900, which are considered to be either very closely related and have sequence homology with C. m. ssp. sepedonicus (Davis, Ann. Rev. Phytopathol. 24:115–140, 1986) or exhibit cross reactivity with anti-C. m. ssp. sepedonicus antisera (De Boer, Phytopathology 72:1474–1477, 1982). Following extraction of DNA by the CTAB method and RNase A treatment, samples containing 125 µg of DNA from each strain were combined (500 µg total). The combined DNA was digested for periods of 2 to 10 min with HaeIII (0.5 Units/µl) in order to establish conditions that yielded DNA fragments with a mean size of approximately 1,000 bp (range 200–4,000 bp). Digested DNA was extracted with an equal volume of chloroform/phenol (1:1 v/v), followed by extraction with an equal volume of chloroform. The DNA was precipitated by addition of 2 volumes of ethanol and the pellet was dissolved in 200 µl double distilled water (ddH$_2$O).

Photobiotinylation of driver DNA. Driver DNA and photobiotin acetate (Sigma, St. Louis, Mo.) were dissolved in distilled water and combined in the ratio 1:2 wt/wt (DNA:photobiotin acetate) and irradiated according to instructions provided with the photobiotinylation kit supplied by (GIBCO-BRL, Gaithersburg, Md.). The pH of the DNA solution was adjusted to pH 9.0 with the addition of 10× TE buffer (final concentration 10 mM Tris-Cl, 1 mM EDTA) and excess photobiotin acetate was extracted with an equal volume of 2-butanol until the butanol was clear. The DNA was then precipitated with ethanol in the presence of 2M ammonium acetate. The efficiency of biotinylation was determined using the BluGene kit according to instructions provided by the supplier (GIBCO-BRL, Gaithersburg, Md.).

Subtraction hybridization. Cms-specific DNA fragments were enriched by subtraction hybridization as outlined in the flow chart shown in FIG. 1. Driver DNA (50 µg) and target DNA (0.7 µg) were combined, precipitated, dried and the pellet was dissolved in 20 µl of 3× SSPE hybridization buffer (20× SSPE is 3.6M NaCl, 200 mM NaH$_2$PO$_4$, 20 mM EDTA pH 7.4; Sambrook et al., 1989), 2.5× Denhardt's, 0.5% SDS and 100 µg/ml denatured salmon sperm DNA. The DNA was denatured at 100° C. for 1 min and reassociated at 68° C. for 48 hr. The solution was cooled to 55° C. with 30 µl of HEPES stock buffer (10 mM HEPES, 1 mM EDTA, pH 7.5).

In order to precipitate any photobiotinylated DNA, subtracting out any tester DNA that had hybridized to homologous driver DNA plus any excess driver DNA, an excess of streptavidin (10 µl at 1 mg/ml) was added and the solution was gently vortexed at room temperature for 10 min. An equal volume of phenol:chloroform (1:1 v/v) was added, the tube was vortexed and centrifuged at 16,000×g. The aqueous layer was removed, and the organic phase was reextracted with 50 µl HEPES. The aqueous phases were combined and 10 µl of streptavidin was added. The mixture was vortexed and extracted with phenol/chloroform and the DNA was precipitated with ethanol at −20° C. This DNA, which was presumed to be enriched for C. m. ssp. sepedonicus-specific sequences, was subjected to two additional rounds of subtraction hybridization, each with the addition of 50 µg of driver DNA, as previously described. DNA which failed to precipitate with the addition of streptavidin following the third round of subtraction was dissolved in 10 µl dH$_2$O and stored at 4° C.

Example 2

Construction of the C. m. ssp. sepedonicus-specific DNA library

PCR Amplification of Unique Tester DNA. Initial attempts to directly clone DNA recovered after subtraction hybridization into the EcoRI site of pUC19 were unsuccessful for undetermined reasons. To enhance the chance of cloning C. m. ssp. sepedonicus-specific DNA, the fragments were amplified by the polymerase chain reaction (PCR) in an Ericomp EZ Cycler (Ericomp, San Diego, Calif.) using a 16-mer primer (SEQ ID NO:1, nucleotides 1–16: 5' AAT-TCCGTTGCTGTCG 3') that is complementary to one strand of the EcoRI adaptor ligated to the termini of each fragment. The reaction buffer included 10 ng of enriched, subtracted C. m. ssp. sepedonicus DNA ("unique tester DNA"), 15–20 pmoles of primer, 200 mM dNTPs (United States Biochemical, Cleveland, Ohio), 1 unit of Taq DNA polymerase (United States Biochemical, Cleveland, Ohio) and 20 mM Tris-Cl buffer (pH 8.3) in a 50 µl reaction volume. The PCR amplification program was 1 cycle of 96° C. for 1 min, 42° C. for 1 min, 72° C. for 2 min, 25 cycles of 96° C. for 1 min, 50° C. for 30 sec, 72° C. for 2 min, and a final annealing and extension step of 72° C. for 10 min.

The PCR products were visualized following agarose gel electrophoresis and ethidium bromide staining. The negative control, with no DNA added, gave no product and the positive control DNA gave the expected 1.2 kb fragment. The amplified unique tester DNA showed a group of fragments of approximately the same size as the DNA fraction used in the subtraction (100–1000 kb).

Cloning of amplified unique tester DNA into pCR1000. The amplified unique tester DNA was subsequently cloned into the T/A cloning vector pCR1000, according to instructions provided by the supplier (Invitrogen, San Diego, Calif.). The pCR1000 library was maintained in E. coli INVαF (Invitrogen, San Diego, Calif.).

Example 3

Hybridization Experiments to Test the Uniqueness of Cms Clones

200 NotI fragments of these clones, containing the insert and a portion of the plasmid, were individually used to probe slot blots containing the plasmid, pCR1000, and DNA extracted from C. m. ssp. sepedonicus (CS3, containing an indigenous plasmid, and P45, lacking plasmid sequences) and five related species: C. m. ssp. insidiosus (CMI), C. m. ssp. rathayi (CMR), C. f. ssp. oortii (CFO), R. fascians (RF), and C. m. ssp. michiganensis (CMM).

Table 1 summarizes the results of probing these slot blots. A number of the clones hybridized to one or both of the C. m. ssp. sepedonicus strains and to none of the related strains.

from the various bacterial species. The DNA was blotted to a Zeta-Probe GT membrane (Bio-Rad, Richmond, Calif.) using 0.4 N NaOH as the transfer solution. Standard protocol hybridization and wash conditions were employed as suggested by the manufacturer).

The Southern blots were hybridized with a $^{32}$P-labelled probe made from Cms50, Cms 72, or Cms 85. All three inserts displayed complete specificity to Cms strains, including P45, a plasmidless Cms strain, and SD1-#2, a non-mucoid Cms strain. Interestingly, only the non-mucoid strain was polymorphic for the DNA sequence that is detected by the Cms50 and Cms72 probes, suggesting that these sequences may be involved in the biosynthesis of extracellular polysaccharide (EPS). These probes did not hybridize with total digested DNA from C. m. ssp. michiganensis, C.

TABLE 1

SELECTED PCR1000 CLONES FOR PROBING DNA SLOT BLOTS

| CLONE # | ~INSERT | pCR1000 | CS3 | P45 | CMI | CMR | CFO | RF | CMM |
|---|---|---|---|---|---|---|---|---|---|
| 5 | 250 bp | + | + | tr | − | − | + | − | − |
| 17 | 250 bp | + | + | − | − | − | − | − | − |
| 40 | 200 bp | + | + | − | − | − | − | − | − |
| 45 | 350 bp | + | + | − | − | − | − | tr | − |
| 50 | 300 bp | + | + | − | − | − | − | − | − |
| 57 | 250 bp | + | + | − | − | − | − | − | − |
| 72 | 250 bp | + | + | + | − | tr | − | tr | tr |
| 75 | 450 bp | + | + | + | − | − | − | − | − |
| 85 | 250 bp | + | + | + | − | tr | − | tr | tr |
| 87 | 350 bp | + | + | tr | − | − | − | − | − |
| 91 | 350 bp | + | + | + | − | tr | − | tr | − |
| 112 | 350 bp | + | + | − | − | − | + | tr | − |
| 126 | 50 bp | + | + | − | − | − | − | − | − |
| 128 | 350 bp | + | + | − | − | − | − | − | − |
| 132 | 250 bp | + | + | tr | − | − | − | − | tr |
| 144 | 100 bp | + | + | − | − | − | − | − | − |
| 149 | 200 bp | + | + | + | + | − | + | + | − |
| 155 | 150 bp | + | + | − | − | − | − | − | − |
| 162 | 200 bp | + | tr | − | − | − | − | − | − |
| 163 | 100 bp | + | + | tr | + | + | + | + | + |

The nucleotide sequences of 16 of these clones was obtained using the dideoxynucleotide chain termination method (Sanger et al., J. Mol. Biol. 98:503–517, 1977). The nucleotide sequence of a number of these clones and for several primers derived from the sequence of these clones is provided in the Sequence Listing. The Cms-specific sequence lies internal to the EcoRI adaptor sequence (5'-AATTCCGTTGCTGTCG-3' (SEQ ID NO:1nucleotides 1–16) or its complement, underlined where shown).

Three inserts, designated Cms50, Cms72 and Cms85, were used to probe Southern blots containing SmaI-digested genomic DNA from a number of strains of Cms and other related species. Plasmid DNA from each of the three clones was extracted using a miniprep procedure (Holmes and Quigley, Anal. Biochem. 114:193–197, 1981). The clones were digested with HindIII and EcoRI, which cut only in the polylinker, leaving 28 and 29 base pairs of vector sequences flanking the adapters attached to the insert, respectively. The released inserts were purified by gel electrophoresis in GTG low gelling temperature agarose (FMC Corp., Rockland, Me.). Slices containing insert DNA were excised from the gel and the insert DNA was labelled with α$^{32}$P-dCTP (New England Nuclear, Boston, Mass.) using the random priming method (Feinberg and Vogelstein, Anal. Biochem. 132:6–13, 1983). The specificity of the labelled insert was determined by hybridization to Southern blots (Southern, J. Mol. Biol. 98:503–517, 1975) containing total digested genomic DNA m. ssp. rathayi, C. m. ssp. insidiosus, Rhodococcus fascians, Curtobacterium flaccumfaciens ssp. ortii, Pseudomonas putida, P. fluorescens, Enterobacter cloacae, Agrobacterium tumefaciens, Erwinia carotovora and Alcaligenes xylosoxidans ssp. denitrificans.

In addition, Cms50 hybridized intensely to Cs3 and P45 DNA, but only faintly to SD1-#2, a nonmucoid Cms strain. It did not hybridize with DNA from the 13 other species. These results indicate that genomic sequences were obtained that are unique to C. m. ssp. sepedonicus. These DNA fragments hybridize to total DNA from strains of C. m. ssp. sepedonicus that harbor an indigenous plasmid and faintly or not at all to DNA from a strain that lacks the plasmid, but not to the DNA from closely related species.

It should be noted that subsequent to these hybridization experiments, Cms163 was shown to be homologous to the ribosomal small subunit RNA. This clone would therefore not be useful as a unique Cms sequence probe or primer, but provides a good positive control.

Example 4

PCR Amplification of DNA from Cms strains and from Related and Unrelated Species An internal oligonucleotide primer set complementary to sequences near the termini of the unique DNA insert of Cms 72 (Forward primer, SEQ ID NO:8; Reverse primer, SEQ ID NO:10) was synthesized using an Applied Biosystems Model 380B synthesizer (Foster City, Calif.). This primer set was used to amplify total genomic DNA from CS3 (Cms), P45 (Cms), 3263 (*Rhodococcus faciens*), 2900 (Cmi), 3224 (Cmm), DSM 60K (Cmm), 2944 (*Curtobacterium flaccumfaciens* subsp. oortii), 2980 (C.m. subsp. rathayi); A (Micrococcus roseus), and several unidentified strains isolated from potato that cross-react with antibodies prepared against Cms (B, B2, and C2).

Genomic DNA homologous to Cms72 DNA can be readily amplified by PCR in Cms strains from forward and reverse primers (20 mers) that are complementary to internal sequences at the termini of Cms72. Moreover, these primers do not amplify a homologous sequence in three strains of *Micrococcus roseus* (obtained from Dr. Sulke De Boer) which were reported to cross-react with antisera made to Cms strain CS3, nor do they amplify a homologous fragment in a limited number of strains of other Clavibacter species described above. These results were confirmed by (1) Southern hybridization experiments using probes derived from Cms 50, Cms72, and Cms85 and (2) PCR using a primer pair derived from Cms72, as summarized in Table 2 below.

TABLE 2

Strains Analyzed by DNA:DNA Hybridization and PCR Using Probes Obtained by Subtraction Hybridization

| | | Method of Detection | | | | |
|---|---|---|---|---|---|---|
| | | DNA:DNA Hybridization:[1] | | | PCR[2] | |
| Species and Strain Number | Distinguishing Features | Cms50 | Cms72 | Cms85 | Cms72 | Source |
| *Clavibacter michiganensis* subsp. *sepedonicus* | | | | | | |
| CS3 | mucoid | + | + | + | + | S. De Boer[a] |
| P45 | mucoid, plasmidless | + | + | + | + | M. Romantschuk[b] |
| SD1#2 | nonmucoid | + | + | + | ND[3] | W. Chun[c] |
| AK14-1 | nonmucoid | − | − | − | ND | W. Chun[c] |
| AK14-2 | nonmucoid | − | − | − | ND | W. Chun[c] |
| 7706a | mucoid | + | + | + | ND | D. Opgenorth[d] |
| 7706c | mucoid | + | + | + | ND | D. Opgenorth[d] |
| 7706e | mucoid | + | + | + | ND | D. Opgenorth[d] |
| 8012 | mucoid | + | + | + | ND | D. Opgenorth[d] |
| 8066b | mucoid | + | + | + | ND | D. Opgenorth[d] |
| 8818a | mucoid | + | + | + | ND | D. Opgenorth[d] |
| 8848c | mucoid | + | + | + | ND | D. Opgenorth[d] |
| 8866c | mucoid | + | + | + | ND | D. Opgenorth[d] |
| 9850 ATCC | mucoid | + | + | + | ND | D. Opgenorth[d] |
| 442 CDFA | mucoid | + | + | + | ND | D. Opgenorth[d] |
| R5 | mucoid | + | + | + | ND | S. De Boer[a] |
| R9 | mucoid | + | + | + | ND | S. De Boer[a] |
| R10 | nonmucoid | − | − | − | ND | S. De Boer[a] |
| R14 | mucoid | + | + | + | ND | S. De Boer[a] |
| subsp. *insidiosum* | | | | | | |
| 2900 | | − | − | − | − | M. Romantschuk[b] |
| 33114 ATCC | | − | − | − | ND | D. Opgenorth[d] |
| 10253 ATCC | | − | − | − | ND | D. Opgenorth[d] |
| subsp. *michiganensis* | | | | | | |
| DSM 60K | yellow | − | − | − | − | F. Neopold[e] |
| 3224 | yellow | − | − | − | − | M. Romantschuk[b] |
| 4450 ATCC | yellow | − | − | − | ND | D. Opgenorth[d] |
| 306 CDFA | yellow | − | − | − | ND | D. Opgenorth[d] |
| 442 CDFA | yellow | − | − | − | ND | D. Opgenorth[d] |
| subsp. *rathayi* | | | | | | |
| 2980 | | − | − | − | − | M. Romantschuk[b] |
| subsp. *tessellarius* | | | | | | |
| 33566 ATCC | | − | − | — | ND | D. Opgenorth[d] |
| *Curtobacterium flaccumfaciens* subsp. *oortii* | | | | | | |
| 2944 | | − | − | − | − | M. Romantschuk[b] |
| *Rhodococcus faciens* | | | | | | |
| 3263 | | − | − | − | − | M. Romantschuk[b] |
| *R. rhodochrous* | | | | | | |
| M2 | | − | − | − | ND | S. De Boer[a] |
| *Micrococcus roseus* | | | | | | |
| A | | ND | ND | ND | − | S. De Boer[a] |
| *Pseudomonas putida* | | | | | | |
| JL4312 | | − | − | − | ND | J. Loper[f] |

TABLE 2-continued

Strains Analyzed by DNA:DNA Hybridization and PCR Using Probes Obtained by Subtraction Hybridization

| | | Method of Detection | | | | |
|---|---|---|---|---|---|---|
| | | DNA:DNA Hybridization:[1] | | | PCR[2] | |
| Species and Strain Number | Distinguishing Features | Cms50 | Cms72 | Cms85 | Cms72 | Source |
| *Pseudomonas fluorescens* | | | | | | |
| JL4094 | | – | – | – | ND | J. Loper[f] |
| *Erwinia carotovora* subsp. *carotovora* | | | | | | |
| LA227 | | – | – | – | ND | J. Loper[f] |
| *Abacterium tumefaciens* | | | | | | |
| K24 | pathogenic | – | – | – | ND | L. Moore[g] |
| k84 | nonpathogenic | – | – | – | ND | L. Moore[g] |
| *Enterobacter cloacae* | | | | | | |
| JL1157 | | – | – | – | ND | J. Loper[g] |
| *Alcaligenes xylosoxidans* subsp. *denitrificans* | | | | | | |
| JL3095 | | – | – | – | ND | J. Loper[f] |
| Unidentified strains[5] | | | | | | |
| B | | ND | ND | ND | – | S. De Boer[a] |
| B2 | | ND | ND | ND | – | S. De Boer[a] |
| C1 | | – | – | – | – | S. De Boer[a] |
| G | | – | – | – | ND | S. De Boer[a] |
| H | | – | – | – | ND | S. De Boer[a] |
| N | | – | – | – | ND | S. De Boer[a] |
| O2 | | – | – | – | ND | S. De Boer[a] |

[a]Agriculture Canada Research Station, Vancouver, Canada
[b]Dept. General Microbiology, University of Helsinki, Helsinki, Finland
[c]Dept. Plant Soil and Entomology, University of Idaho, Moscow, I
[d]California Department of Food and Agriculture, Sacramento, CA
[e]Institut fur Pflanzenschutz in Ackerbau und Grunlan, Messeweg 11/12, D-3000 Braunschweig, Germany
[f]USDA ARS, Horticultural Crops Laboratory, Corvallis, OR
[g]Department of Botany and Plant Pathology, Oregon State University, Corvallis, OR
[1] $^{32}$P probes made of Cms50, Cms72 and Cms85 and hybridized with SmaI digested genomic DNA
[2]Hybridization of $^{32}$P Cms probe to PCR amplification products obtained with primers complementary to internal sequences near termini
[3]Identified as *C. m.* subsp. *sepedonicus* (Cms) by other criteria
[4]ND = Not Determined
[5]Strains that cross-react with antibodies to Cms but do not have properties of Cms Example 5

PCR Amplification of DNA from Non-Mucoid Cms Strains

Variation of PCR products from non-mucoid Cms strains. Southern blotted, digested genomic DNA from non-mucoid strains AK14-1 and AK14-2 does not hybridize with radio-labelled Cms 50, Cms 72, or Cms 85 DNA probes. Attempts to obtain genomic DNA from these strains for Southern blot analysis using several extraction methods has proven difficult because they grow poorly and resist standard lysis procedures.

Although it was thought possible that the lack of a hybridization signal resulted from partial degradation of the DNA from AK14-1 and AK14-2, the PCR amplification procedure described above was used to assay for homology between Cms 85 and sequences in the genomes of these two non-mucoid strains. A Cms 85 primer set (Forward primer, SEQ ID NO:13; Reverse primer, SEQ ID NO:14) synthesized on an Applied Biosystems Model 380B synthesizer (Foster City, Calif.) was employed.

In all mucoid strains and in non-mucoid strain SD1#2, PCR amplification produced a single 205 bp PCR product that was homologous to Cms 85. By contrast, amplification of genomic DNA from both AK14-1 and AK14-2 resulted in a pair of PCR products of approximately 150 bp (designated Cms 85-1) and 240 bp (designated Cms 85-2). These PCR products were gel purified and found to hybridize only very weakly with the Cms 85 probe, suggesting that their homology with Cms 85 is limited to the common primer sequences. When sequenced as described above, the 142 bp Cms 85-1 sequence (SEQ ID NO:29) showed no regions of significant homology with Cms 85.

Cms 85-1 was radiolabelled and used to probe a Southern blot of digested genomic DNA from Cms and other species. The Cms 85-1 probe hybridized specifically with genomic DNA from both non-mucoid and mucoid strains of Cms. It did not hybridize with genomic DNA from 26 strains representing 17 other bacterial species.

Genomic location of Cms 85 and Cms 85-1. Both Cms 85 and Cms 85-1 PCR products hybridized to a SmaI fragment of approximately 3.5 kb in the genome of strain Cs3. The fact that the Cms 85 primer set amplifies only the Cms 85 sequence from Cs3 genomic DNA indicates that no other primer sites are positioned closely enough in the genome of Cs3 (and other mucoid strains) to produce additional PCR products under the PCR conditions used. However, in the non-mucoid strains AK14-1 and AK14-2, the Cms 85-1 PCR product, at least, appears to have resulted from amplification of a region adjacent to Cms 85. One or both of the primer sites from which Cms 85 DNA is amplified in all mucoid wild-type strains appear to be different than the sites from which Cms 85-1 and Cms 85-2 sequences are amplified in the non-mucoid variants AK14-1 and AK14-2. In AK14-1 and AK14-2 other complete or partial sequences were recognized by the Cms 85 primer set and amplified to produce the Cms 85-1 and Cms 85-2 products. It is therefore likely that there are multiple copies of one or both of the Cms 85 primer sites on a SmaI fragment in the genome of wild-type strains.

It was not possible to determine by Southern analysis whether the 3.5 kb SmaI fragment is present in non-mucoid Cms strains for the reasons discussed above.

Consequences of putative deletions and rearrangements. The non-mucoid phenotype could arise in some strains by deletion or gross chromosome rearrangement(s), since a (1) restriction fragment length polymorphism (RFLP) was observed when both Cms 50 and Cms 72 were used to prove genomic DNA fragments from another non-mucoid strain SD1#2, and (2) no homologous sequences in AK1-1 and AK1-2 could be detected with probes made from Cms 50, Cms 72, or Cms 85. Such deletions or rearrangements can result in the repositioning of other copies of the primer sequences, making them spatially suited to serve as sites for amplification of new DNA sequences. Even though Cms 85-1 and Cms 85-2 lack homology with Cms 85, they likely represent regions adjacent to and thus closely linked to Cms 85. These results demonstrate that sequences flanking other unique Cms sequences obtained through genomic subtraction are also likely to be highly species-specific.

All publications and published patent documents cited in this specification are incorporated herein by reference to the same extent as if each individual publication or patent application was specifically and individually indicated to be incorporated by reference.

This invention has been detailed both by example and by direct description. It should be apparent that one having ordinary skill in this art would be able to surmise equivalents to the invention as described in the claims which follow but which would be within the spirit of the description above. Those equivalents are to be included within the scope of this invention.

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 246 base pairs
        ( B ) TYPE: Nucleic acid
        ( C ) STRANDEDNESS: Double stranded
        ( D ) TOPOLOGY: Linear ( i i ) MOLECULE TYPE:
        ( A ) DESCRIPTION: Genomic DNA ( v i ) ORIGINAL SOURCE:
        ( A ) ORGANISM: Clavibacter michiganensis ssp.
            sepedonicus (Cms)
        ( B ) STRAIN: Cs3

( v i i ) IMMEDIATE SOURCE:
        ( A ) LIBRARY: Genomic
        ( B ) CLONE: Cms 17

( i x ) FEATURE:
        ( A ) NAME/KEY: EcoRI adaptor sequence
        ( B ) LOCATION: Underlined
        ( C ) IDENTIFICATION METHOD: Similarity to known
            sequence ( x i ) SEQUENCE DESCRIPTION: SEQ ID NO:1:

```
AATTCCGTTG  CTGTCGCTGG  GCGGACGACG  GCGCGACGAT  GAGGGGAGTC      50

AGGCAGGTCA  GTGTTACCGC  TGCGCAGGCG  ATGAGCAGAC  GTGCTGATCG     100

AGAGGTAAGC  GAGTGATGTG  TGCGCAACAA  TCAAGTTCTC  CAATAACCCT     150

TTTAGGGACT  ATCCTGAGCC  GTTGACACCA  GGTGAAGGTG  TTGTTGATGT     200

CCGTAAACGG  CGGAAGGTTC  ATTTATGCTT  CGACAGCAAC  GGAATT         246
```

( 2 ) INFORMATION FOR SEQ ID NO:2:

( i ) SEQUENCE CHARACTERISTICS:
        ( A ) LENGTH: 313 base pairs (B) TYPE: Nucleic acid
                (C) STRANDEDNESS: Double stranded
                (D) TOPOLOGY: Linear (ii) MOLECULE TYPE:
                (A) DESCRIPTION: Genomic DNA (vi) ORIGINAL SOURCE:
                (A) ORGANISM: Clavibacter michiganensis ssp.
                    sepedonicus (Cms)
                (B) STRAIN: Cs3

(vii) IMMEDIATE SOURCE:
                (A) LIBRARY: Genomic
                (B) CLONE: Cms 45

(ix) FEATURE:
                (A) NAME/KEY: EcoRI adaptor sequence
                (B) LOCATION: Underlined
                (C) IDENTIFICATION METHOD: Similarity to known
                    sequence (xi) SEQUENCE DESCRIPTION: SEQ ID NO:2:

```
AATTCCGTTG CTGTCGAACC AATTCGAGCT GATCGTGGAC ACCACGAACA    50

TGGAAACGAG CATGAACAGG AATATCAGCA ACGGGTGGCC GATGAGCGTA   100

GGAGCACACA CGCCGACAAT NTTCAACGCG AACGTCCNCC GGTNCTTGTC   150

AATAACCCAC ATGACCCCAA CNNGTACNTG TCCGNCCATN AAATNCNGCT   200

TGANNTATNN ATTGTTNCTN GCATTATCTN ATGNNGTNAT NTCATGGGNG   250

NACTNNTACC GNTTTGGGTC ATGTGGTTAN TTGACAAAGA CCGNNGAGNT   300

TGTTTTAAAA TTT                                          313
```

(2) INFORMATION FOR SEQ ID NO:3:

(i) SEQUENCE CHARACTERISTICS:
                (A) LENGTH: 224 base pairs
                (B) TYPE: Nucleic Acid
                (C) STRANDEDNESS: Double stranded
                (D) TOPOLOGY: Linear (ii) MOLECULE TYPE:
                (A) DESCRIPTION: Genomic DNA (vi) ORIGINAL SOURCE:
                (A) ORGANISM: Clavibacter michiganensis ssp.
                    sepedonicus (Cms)
                (B) STRAIN: Cs3

(vii) IMMEDIATE SOURCE:
                (A) LIBRARY: Genomic
                (B) CLONE: Cms 50

(xi) SEQUENCE DESCRIPTION: SEQ ID NO:3:

```
CCGGAGCGCG ATAGAAGAGG AACTCTTTGT CAATAATGCT GATAACGTGA    50

TCAAGGAAGT CGTCGGATGA AGATGCGACA TGGCTCCTCG GTCCTTGAAT   100

GTCCGCGGCT TTTGCCAGAT TCAGGTCACC ACGGTACTGA GCGATGCTCT   150

GCCAAGTGAT GACCCCGTGC ATATTTTTCT TGTCGTTGCT CAGGACTGGC   200

ACCTGAGAGA TGTCCTTCAT GATC                              224
```

(2) INFORMATION FOR SEQ ID NO:4:

(i) SEQUENCE CHARACTERISTICS:
                (A) LENGTH: 22 nucleotides
                (B) TYPE: Nucleic acid
                (C) STRANDEDNESS: Single stranded
                (D) TOPOLOGY: Linear ( i i ) MOLECULE TYPE:
    ( A ) DESCRIPTION: Other nucleic acid
        ( oligonucleotide )

( v i ) ORIGINAL SOURCE:
    ( A ) ORGANISM: Clavibacter michiganensis ssp.
        sepedonicus (Cms)
    ( B ) STRAIN: Cs3

( v i i ) IMMEDIATE SOURCE:
    ( A ) LIBRARY: Genomic
    ( B ) CLONE: Cms 50 (Oligonucleotide chemically
        synthesized to correspond to
        nucleotides 4-25 of SEQ ID. NO:3)

( x i ) SEQUENCE DESCRIPTION: SEQ ID NO:4:

GAGCGCGATA GAAGAGGAAC TC                                      22

( 2 ) INFORMATION FOR SEQ ID NO:5:

( i ) SEQUENCE CHARACTERISTICS:
        ( A ) LENGTH: 22 nucleotides
        ( B ) TYPE: Nucleic acid
        ( C ) STRANDEDNESS: Single stranded
        ( D ) TOPOLOGY: Linear ( i i ) MOLECULE TYPE:
        ( A ) DESCRIPTION: Other nucleic acid
            ( oligonucleotide )

( v i ) ORIGINAL SOURCE:
        ( A ) ORGANISM: Clavibacter michiganensis ssp.
            sepedonicus (Cms)
        ( B ) STRAIN: Cs3

( v i i ) IMMEDIATE SOURCE:
        ( A ) LIBRARY: Genomic
        ( B ) CLONE: Cms 50 (Oligonucleotide chemically
            synthesized to be complementary to
            nucleotides 196-175 of SEQ ID. NO:3)

( x i ) SEQUENCE DESCRIPTION: SEQ ID NO:5:

GTCCTGAGCA ACGACAAGAA AA                                      22

( 2 ) INFORMATION FOR SEQ ID NO:6:

( i ) SEQUENCE CHARACTERISTICS:
        ( A ) LENGTH: 220 base pairs
        ( B ) TYPE: Nucleic acid
        ( C ) STRANDEDNESS: Double stranded
        ( D ) TOPOLOGY: Linear ( i i ) MOLECULE TYPE:
        ( A ) DESCRIPTION: Genomic DNA ( v i ) ORIGINAL SOURCE:
        ( A ) ORGANISM: Clavibacter michiganensis ssp.

```
GACAGCCGAC AGCTTGCACA CTACGAGTCG AGTGGTCCTC CACCCTGAGG    150

TGCTTGCTCA GAGCTTGCTG CTAACTTGCT GCTGGCAATA CGACAGCAAT    200

ACGGCGACAG CAACGGAATT                                      220
```

( 2 ) INFORMATION FOR SEQ ID NO:7:

( i ) SEQUENCE CHARACTERISTICS:
        ( A ) LENGTH: 247 base pairs
        ( B ) TYPE: Nucleic acid
        ( C ) STRANDEDNESS: Double stranded
        ( D ) TOPOLOGY: Linear ( i i ) MOLECULE TYPE:
        ( A ) DESCRIPTION: Genomic DNA ( v i ) ORIGINAL SOURCE:
        ( A ) ORGANISM: Clavibacter michiganensis ssp.
            sepedonicus (Cms)
        ( B ) STRAIN: Cs3

( v i i ) IMMEDIATE SOURCE:
        ( A ) LIBRARY: Genomic
        ( B ) CLONE: Cms 72

( x i ) SEQUENCE DESCRIPTION: SEQ ID NO:7:

```
TAGGAACGAA GATGTACTTT CCCTACTTTC GCGGTAAGCA GTTCGAGTTG    50

ATAGCAATCC GCGAGTCAGC GGCGGTCATC GCAGACGCAG GTTTCAATCC    100

GATCATCGAG CCGGTTCGCG AGACCTTCAA AGGACTTCAG CGCACCTTAG    150

ACGAACTGCT CCTGAACGGG GCCAAAGCCA CGGTGATCGT GAATCCGAGA    200

CACGGTGACC ACAGGGATAG CAGCGAAATT CTTGCACAAT ACATGGC       247
```

( 2 ) INFORMATION FOR SEQ ID NO:8:

( i ) SEQUENCE CHARACTERISTICS:
        ( A ) LENGTH: 20 nucleotides
        ( B ) TYPE: Nucleic acid
        ( C ) STRANDEDNESS: Single stranded
        ( D ) TOPOLOGY: Linear ( i i ) MOLECULE TYPE:
        ( A ) DESCRIPTION: Other nucleic acid
            ( oligonucleotide )

( v i ) ORIGINAL SOURCE:
        ( A ) ORGANISM: Clavibacter michiganensis ssp.
            sepedonicus (Cms)
        ( B ) STRAIN: Cs3

( v i i ) IMMEDIATE SOURCE:
        ( A ) LIBRARY: Genomic
        ( B ) CLONE: Cms 72 (Oligonucleotide chemically
            synthesized to correspond to
            nucleotides 26-45 of SEQ ID. NO:7)

( x i ) SEQUENCE DESCRIPTION: SEQ ID NO:8:

```
CTTTCGCGGT AAGCAGTTCG                                      20
```

( 2 ) INFORMATION FOR SEQ ID NO:9:

( i ) SEQUENCE CHARACTERISTICS:
( A ) LENGTH: 23 nucleotides
( B ) TYPE: Nucleic acid
( C ) STRANDEDNESS: Single stranded
( D ) TOPOLOGY: Linear ( i i ) MOLECULE TYPE:
( A ) DESCRIPTION: Other nucleic acid (oligonucleotide)

-continued ( v i ) ORIGINAL SOURCE:
  ( A ) ORGANISM: Clavibacter michiganensis ssp.
    sepedonicus (Cms)
  ( B ) STRAIN: Cs3

( v i i ) IMMEDIATE SOURCE:
  ( A ) LIBRARY: Genomic
  ( B ) CLONE: Cms 72 (Oligonucleotide chemically
    synthesized to correspond to
    nucleotides 40-62 of SEQ ID. NO:7)

( x i ) SEQUENCE DESCRIPTION: SEQ ID NO:9:

AGTTCGAGTT GATAGCAATC CGC                      23

( 2 ) INFORMATION FOR SEQ ID NO:10:

( i ) SEQUENCE CHARACTERISTICS:
  ( A ) LENGTH: 20 nucleotides
  ( B ) TYPE: Nucleic acid
  ( C ) STRANDEDNESS: Single stranded
  ( D ) TOPOLOGY: Linear ( i i ) MOLECULE TYPE:
  ( A ) DESCRIPTION: Other nucleic acid
    ( o l i g o n u c l e o t i d e )

( v i ) ORIGINAL SOURCE:
  ( A ) ORGANISM: Clavibacter michiganensis ssp.
    sepedonicus (Cms)
  ( B ) STRAIN: Cs3

( v i i ) IMMEDIATE SOURCE:
  ( A ) LIBRARY: Genomic
  ( B ) CLONE: Cms 72 (Oligonucleotide chemically
    synthesized to be complementary to
    nucleotides 228-209 of SEQ ID. NO:7)

( x i ) SEQUENCE DESCRIPTION: SEQ ID NO:10:

TTTCGCTGCT ATCCCTGTGG                      20

( 2 ) INFORMATION FOR SEQ ID NO:11:

( i ) SEQUENCE CHARACTERISTICS:
  ( A ) LENGTH: 310 base pairs
  ( B ) TYPE: Nucleic acid
  ( C ) STRANDEDNESS: Double stranded
  ( D ) TOPOLOGY: Linear ( i i ) MOLECULE TYPE:
  ( A ) DESCRIPTION: Genomic DNA ( v i ) ORIGINAL SOURCE:
  ( A ) ORGANISM: Clavibacter michiganensis ssp.
    sepedonicus (Cms)
  ( B ) STRAIN: Cs3

( v i i ) IMMEDIATE SOURCE:
  ( A ) LIBRARY: Genomic
  ( B ) CLONE: Cms 75

( i x ) FEATURE:
  ( A ) NAME/KEY: EcoRI adaptor sequence
  ( B ) LOCATION: Underlined
  ( C ) IDENTIFICATION METHOD: Similarity to known
    sequence ( x i ) SEQUENCE DESCRIPTION: SEQ ID NO:11:

AATTCCGTTG CTGTCGTGTG TGCATCCCCT GGGCGAATGG GGTGTGGCTC  50

CTTCCGGTGG TCGGGCTGTG CTGACATCTA CTAACCTACC CAGCCCGGGC  100

GAAGGTGTCA ACCCCCTTAG GTCACACCGT CTGGTTCCCT CCTTCCTCTT  150

GGTGCGGCGG TCGGCCAGGA AGGGGGTGGC ATGTGCCAAC CCCTCGATGC  200

```
GCTAGGCGAA GCTGGTGTGG ATTTCGTCCA CGTCCCAGCG GTCCGCGCCG    250

TTTTCGCGGA GGGAGTCCAG GAGCGAACCG GTTGAGATTT CGGCCGACAG    300

CAACGGAATT                                                310
```

(2) INFORMATION FOR SEQ ID NO:12:

(i) SEQUENCE CHARACTERISTICS:
        (A) LENGTH: 232 base pairs
        (B) TYPE: Nucleic acid
        (C) STRANDEDNESS: Double stranded
        (D) TOPOLOGY: Linear (ii) MOLECULE TYPE:
        (A) DESCRIPTION: Genomic DNA (vi) ORIGINAL SOURCE:
        (A) ORGANISM: Clavibacter michiganensis ssp.
            sepedonicus (Cms)
        (B) STRAIN: Cs3

(vii) IMMEDIATE SOURCE:
        (A) LIBRARY: Genomic
        (B) CLONE: Cms 85

(xi) SEQUENCE DESCRIPTION: SEQ ID NO:12:

```
GAAGATCAGA AGCGACCCGC CATGCTGTCG CACTCTCGAC AGAGAAAGCG     50

AGTCCGCTTT GGCTGTGGAT TCCGGCTCGG TCGTAAGCAG CCTCGAGGTC    100

CTGGGCTTCG GGCTAAGCCA GGTCTTTCCA GGCATCCTGT TCCGTCTGGG    150

TCTTTAGCGC GTAGTCCTGA ACTTCAGCCG CAGTCGGGCT GGATTTGGCT    200

GTGCGAGCCG ACGAGGATGC GCTGACGGCA TA                       232
```

(2) INFORMATION FOR SEQ ID NO:13:

(i) SEQUENCE CHARACTERISTICS:
        (A) LENGTH: 20 nucleotides
        (B) TYPE: Nucleic acid
        (C) STRANDEDNESS: Single stranded
        (D) TOPOLOGY: Linear (ii) MOLECULE TYPE:
        (A) DESCRIPTION: Other nucleic acid
            (oligonucleotide)

(vi) ORIGINAL SOURCE:
        (A) ORGANISM: Clavibacter michiganensis ssp.
            sepedonicus (Cms)
        (B) STRAIN: Cs3

(vii) IMMEDIATE SOURCE:
        (A) LIBRARY: Genomic
        (B) CLONE: Cms 85 (Oligonucleotide chemically
            synthesized to correspond to
            nucleotides 2-21 of SEQ ID. NO:12)

(xi) SEQUENCE DESCRIPTION: SEQ ID NO:13:

```
AAGATCAGAA GCGACCCGCC                                      20
```

(2) INFORMATION FOR SEQ ID NO:14:

(i) SEQUENCE CHARACTERISTICS:
        (A) LENGTH: 19 nucleotides
        (B) TYPE: Nucleic acid
        (C) STRANDEDNESS: Single stranded
        (D) TOPOLOGY: Linear (ii) MOLECULE TYPE:
        (A) DESCRIPTION: Other nucleic acid
            (oligonucleotide)

( v i ) ORIGINAL SOURCE:
    ( A ) ORGANISM: Clavibacter michiganensis ssp.
        sepedonicus (Cms)
    ( B ) STRAIN: Cs3

( v i i ) IMMEDIATE SOURCE:
    ( A ) LIBRARY: Genomic
    ( B ) CLONE: Cms 85 (Oligonucleotide chemically
        synthesized to be complementary to
        nucleotides 206-188 of SEQ ID. NO:12)

( x i ) SEQUENCE DESCRIPTION: SEQ ID NO:14:

TCGCACAGCC AAATCCAGC                                                         19

( 2 ) INFORMATION FOR SEQ ID NO:15:

( i ) SEQUENCE CHARACTERISTICS:
        ( A ) LENGTH: 346 base pairs
        ( B ) TYPE: Nucleic acid
        ( C ) STRANDEDNESS: Double stranded
        ( D ) TOPOLOGY: Linear ( i i ) MOLECULE TYPE:
        ( A ) DESCRIPTION: Genomic DNA ( v i ) ORIGINAL SOURCE:
        ( A ) ORGANISM: Clavibacter michiganensis ssp.
            sepedonicus (Cms)
        ( B ) STRAIN: Cs3

( v i i ) IMMEDIATE SOURCE:
        ( A ) LIBRARY: Genomic
        ( B ) CLONE: Cms 87

( i x ) FEATURE:
        ( A ) NAME/KEY: EcoRI adaptor sequence
        ( B ) LOCATION: Underlined
        ( C ) IDENTIFICATION METHOD: Similarity to known
            sequence ( x i ) SEQUENCE DESCRIPTION: SEQ ID NO:15:

AATTCCGTTG CTGTCGGCTG TCGAAACCTG TGAAGCTAAT CCCAGTGCCA          50

TACAGGGGCC ACATATCCTC TAGTTACTCC CCGTGATGAA GGGTGAAGAC         100

CCTAGGGGAT TATGCGTAAG GCGTTGTAGA CCTTCCTCCA CCCCCTCGCG 150

CTCCTCCGCC TCCATGACTC GGAACGACTC GAGATCGAGC GACATAATGT 200

TCAAAACATG AATGAATTTT TCAACGGATA CCGTTTCTAT GGCCTGAGCA 250

AAAATAGGAC GATGCAAGTC CTTGATTGTG AGAACACCCT TGCCTATTTG 300

GAACATAAGG GAGAGATTCA TAAGGTTATA CGACAGCAAC GGAATT 346

( 2 ) INFORMATION FOR SEQ ID NO:16:

( i ) SEQUENCE CHARACTERISTICS:
( A ) LENGTH: 328 base pairs
( B ) TYPE: Nucleic acid
( C ) STRANDEDNESS: Double stranded
( D ) TOPOLOGY: Linear ( i i ) MOLECULE TYPE:
( A ) DESCRIPTION: Genomic DNA ( v i ) ORIGINAL SOURCE:
( A ) ORGANISM: Clavibacter michiganensis ssp. sepedonicus (Cms)
( B ) STRAIN: Cs3

( v i i ) IMMEDIATE SOURCE:
( A ) LIBRARY: Genomic
( B ) CLONE: Cms 91

( i x ) FEATURE:

(A) NAME/KEY: EcoRI adaptor sequence
(B) LOCATION: Underlined
(C) IDENTIFICATION METHOD: Similarity to known sequence (x i) SEQUENCE DESCRIPTION: SEQ ID NO:16:

| | | | | | |
|---|---|---|---|---|---|
| AATTCCGTTG | CTGTCGGTTA | CCAAGAGAAC | CAAGCCAGTC | GGTTGCNTTG | 50 |
| GTAATAATTG | GGGCTGCGTA | AAGCATGTTT | TGGTGACGCG | ACTTACAAAG | 100 |
| AGCCGAGGAG | AGAGTCGCTG | AATAATGCTG | ANTCGGATGC | GAGCACTGGG | 150 |
| GCGCTCCTGC | GCAAGTGAGC | GTGCGACAAC | ACCACTGCCG | GAAAACAGGT | 200 |
| CTACCGCAAC | TTTACCGGGC | GAAGGACCGC | TCTCTACCGC | GGACGAAATT | 250 |
| TCAGCTAAAT | AGCGCGTCTT | ATTACCCAGG | TAGTGAATTG | GCCTCATGCC | 300 |
| AGATTCGTCG | TTCGACAGCA | ACGGAATT | | | 328 |

(2) INFORMATION FOR SEQ ID NO:17:

(i) SEQUENCE CHARACTERISTICS:
 (A) LENGTH: 239 base pairs
 (B) TYPE: Nucleic acid
 (C) STRANDEDNESS: Double stranded
 (D) TOPOLOGY: Linear (i i) MOLECULE TYPE:
 (A) DESCRIPTION: Genomic DNA (v i) ORIGINAL SOURCE:
 (A) ORGANISM: Clavibacter michiganensis ssp. sepedonicus (Cms)
 (B) STRAIN: Cs3

(v i i) IMMEDIATE SOURCE:
 (A) LIBRARY: Genomic
 (B) CLONE: Cms 126

(i x) FEATURE:
 (A) NAME/KEY: EcoRI adaptor sequence
 (B) LOCATION: Underlined
 (C) IDENTIFICATION METHOD: Similarity to known sequence (x i) SEQUENCE DESCRIPTION: SEQ ID NO:17:

| | | | | | |
|---|---|---|---|---|---|
| AATTCCGTTG | CTGTCGTCCC | TGCGACAGGG | AATGGCCCGN | TCAAAGTTGC | 50 |
| TNTAAGGAAG | GCGCAAAACA | ATCTTGCCAA | TGGCGCGAGG | NGTGAATNAC | 100 |
| TGAATGNTAC | TGCAGCGGGC | GGCCCCACTG | TNGGTCGGGN | CACACTGTGT | 150 |
| GTTTCTATGT | GATTCAGGNT | TTACGGNGAT | GAGTTCCAGA | TCTCGNTCCN | 200 |
| GNGACGTCCA | GGNCACCNTT | CCCCGACAGC | AACGGAATT | | 239 |

(2) INFORMATION FOR SEQ ID NO:18:

(i) SEQUENCE CHARACTERISTICS:
 (A) LENGTH: 394 base pairs
 (B) TYPE: Nucleic acid
 (C) STRANDEDNESS: Double stranded
 (D) TOPOLOGY: Linear (i i) MOLECULE TYPE:
 (A) DESCRIPTION: Genomic DNA (v i) ORIGINAL SOURCE:
 (A) ORGANISM: Clavibacter michiganensis ssp. sepedonicus (Cms)
 (B) STRAIN: Cs3

(v i i) IMMEDIATE SOURCE:
 (A) LIBRARY: Genomic
 (B) CLONE: Cms 128

(ix) FEATURE:
    (A) NAME/KEY: EcoRI adaptor sequence
    (B) LOCATION: Underlined
    (C) IDENTIFICATION METHOD: Similarity to known
        sequence (xi) SEQUENCE DESCRIPTION: SEQ ID NO:18:

```
AATTCCGTTG CTGTCGTGCT TCGCAGTAAA CGACCCGAGC ACGGCGTCGT      50
CTCAGCAGGG ACCCCGTTTC ATATTTCTAC GACGAACGGA TTGTGGGCCG     100
TGGGTGCGGA CTCGTCGGCG GATCAAGTGA CGGTAAATCT CGCTGCTGGG     150
TATGTCGTCG ATGGCGCCCT CAGTCCCTCC AAGGTCGCAG GAATTGCACT     200
TGTTATGAAG TGGTCAAATG GTGCCTGGCA TGTTTTGAGT GGCAAATTGC     250
TCGACCAGAA CCTGCTCGCG CAGGGTGGAA TCCGTTATAC GGGAGGGTGC     300
TGATGGCAAG CGAATGCGAC CGCGGGACCT CTTGGGTGTG CAGGTCAGGC     350
TATTGGCGAT GCGGTCAAGG ACACCCATCG ACAGCAACGG AATT           394
```

(2) INFORMATION FOR SEQ ID NO:19:

(i) SEQUENCE CHARACTERISTICS:
        (A) LENGTH: 242 base pairs
        (B) TYPE: Nucleic acid
        (C) STRANDEDNESS: Double stranded
        (D) TOPOLOGY: Linear (ii) MOLECULE TYPE:
        (A) DESCRIPTION: Genomic DNA (vi) ORIGINAL SOURCE:
        (A) ORGANISM: Clavibacter michiganensis ssp.
            sepedonicus (Cms)
        (B) STRAIN: Cs3

(vii) IMMEDIATE SOURCE:
        (A) LIBRARY: Genomic
        (B) CLONE: Cms 132

(ix) FEATURE:
        (A) NAME/KEY: EcoRI adaptor sequence
        (B) LOCATION: Underlined
        (C) IDENTIFICATION METHOD: Similarity to known
            sequence (xi) SEQUENCE DESCRIPTION: SEQ ID NO:19:

```
AATTCCGTTG CTGTCGTTAC AGGACGAACG AGCACGGACA CATCGACCGT      50
GTCATCATCC AGGATCTGCA GCTCAAGACC CATGAAGGAC GTCTTCCGCA     100
TCAAAGAAAT CCTGTGGGCA AGCTCCAGGG GGATCATGCG GGACATCTCG     150
CCGCGGACGC TGCCGGGGGC TCTCCGAAGC TGGACAACAT CGTCGCGATG     200
TCCCAAAAGA ACAACCTGGT AGAATACGAC AGCAACGGAA TT             242
```

(2) INFORMATION FOR SEQ ID NO:20:

(i) SEQUENCE CHARACTERISTICS:
        (A) LENGTH: 90 base pairs
        (B) TYPE: Nucleic acid
        (C) STRANDEDNESS: Double stranded
        (D) TOPOLOGY: Linear (ii) MOLECULE TYPE:
        (A) DESCRIPTION: Genomic DNA (vi) ORIGINAL SOURCE:
        (A) ORGANISM: Clavibacter michiganensis ssp.
            sepedonicus (Cms)
        (B) STRAIN: Cs3

( v i i ) IMMEDIATE SOURCE:
    ( A ) LIBRARY: Genomic
    ( B ) CLONE: Cms 144

( i x ) FEATURE:
    ( A ) NAME/KEY: EcoRI adaptor sequence
    ( B ) LOCATION: Underlined
    ( C ) IDENTIFICATION METHOD: Similarity to known
        sequence ( x i ) SEQUENCE DESCRIPTION: SEQ ID NO:20:

```
AATTCCGTTG  CTGTCGAGGG  GGCAATCATC  ATTGCGGCAT  TGCCCCTCGG      50

CACGATTCCC  TGCAACATTC  GAGACGACAG  CAACGGAATT                  90
```

( 2 ) INFORMATION FOR SEQ ID NO:21:

( i ) SEQUENCE CHARACTERISTICS:
        ( A ) LENGTH: 245 base pairs
        ( B ) TYPE: Nucleic acid
        ( C ) STRANDEDNESS: Double stranded
        ( D ) TOPOLOGY: Linear ( i i ) MOLECULE TYPE:
        ( A ) DESCRIPTION: Genomic DNA ( v i ) ORIGINAL SOURCE:
        ( A ) ORGANISM: Clavibacter michiganensis ssp.
            sepedonicus (Cms)
        ( B ) STRAIN: Cs3

( v i i ) IMMEDIATE SOURCE:
        ( A ) LIBRARY: Genomic
        ( B ) CLONE: Cms 149

( x i ) SEQUENCE DESCRIPTION: SEQ ID NO:21:

```
GTTTGTAAGC  AAACGGTTTC  AGGTACTATT  TCACTCCCCT  CCCGGGGTAC      50

TTTTCACCTT  TCCCTCACGG  TACTTGTCCG  CTATCGGTCA  TCTGGGAGTA     100

TTTAGGCTTA  TCAGGTGGTC  CTGACAGATT  CACACGGGAT  TTCTCGGGCC     150

CCGTGCTACT  TGGGATACTC  TCCGGACAGG  CGACGACATT  TCGACTACGG     200

GGTTCGCACC  CTCTATGACT  GGCCTTTCAA  GACCATTCGT  CAATA          245
```

( 2 ) INFORMATION FOR SEQ ID NO:22:

( i ) SEQUENCE CHARACTERISTICS:
        ( A ) LENGTH: 24 nucleotides
        ( B ) TYPE: Nucleic acid
        ( C ) STRANDEDNESS: Single stranded
        ( D ) TOPOLOGY: Linear ( i i ) MOLECULE TYPE:
        ( A ) DESCRIPTION: Other nucleic acid
            ( o l i g o n u c l e o t i d e )

( v i ) ORIGINAL SOURCE:
        ( A ) ORGANISM: Clavibacter michiganensis ssp.
            sepedonicus (Cms)
        ( B ) STRAIN: Cs3

( v i i ) IMMEDIATE SOURCE:
        ( A ) LIBRARY: Genomic
        ( B ) CLONE: Cms 149 (Oligonucleotide chemically
            synthesized to correspond to
            nucleotides 18-41 of SEQ ID. NO:21)

( x i ) SEQUENCE DESCRIPTION: SEQ ID NO:22:

```
TTCAGGTACT  ATTTCACTCC  CCTC                                    24
```

( 2 ) INFORMATION FOR SEQ ID NO:23:

-continued ( i ) SEQUENCE CHARACTERISTICS:
( A ) LENGTH: 22 nucleotides
( B ) TYPE: Nucleic acid
( C ) STRANDEDNESS: Single stranded
( D ) TOPOLOGY: Linear ( i i ) MOLECULE TYPE:
( A ) DESCRIPTION: Other nucleic acid
( o l i g o n u c l e o t i d e )

( v i ) ORIGINAL SOURCE:
( A ) ORGANISM: Clavibacter michiganensis ssp. sepedonicus (Cms)
( B ) STRAIN: Cs3

( v i i ) IMMEDIATE SOURCE:
( A ) LIBRARY: Genomic
( B ) CLONE: Cms 149 (Oligonucleotide chemically synthesized to be complementary to nucleotides 228-207 of SEQ ID. NO:21)

( x i ) SEQUENCE DESCRIPTION: SEQ ID NO:23:

GAAAGGCCAG TCATAGAGGG TG 22

( 2 ) INFORMATION FOR SEQ ID NO:24:

( i ) SEQUENCE CHARACTERISTICS:
( A ) LENGTH: 168 base pairs
( B ) TYPE: Nucleic acid
( C ) STRANDEDNESS: Double stranded
( D ) TOPOLOGY: Linear ( i i ) MOLECULE TYPE:
( A ) DESCRIPTION: Genomic DNA ( v i ) ORIGINAL SOURCE:
( A ) ORGANISM: Clavibacter michiganensis ssp. sepedonicus (Cms)
( B ) STRAIN: Cs3

( v i i ) IMMEDIATE SOURCE:
( A ) LIBRARY: Genomic
( B ) CLONE: Cms 155

( i x ) FEATURE:
( A ) NAME/KEY: EcoRI adaptor sequence
( B ) LOCATION: Underlined
( C ) IDENTIFICATION METHOD: Similarity to known sequence ( x i ) SEQUENCE DESCRIPTION: SEQ ID NO:24:

AATTCCGTTG CTGTCGCTGG AACTCATCAC CGTAAACCCT GAATCACATA 50

GAAACACACA GTGTGGCCCG ACCCACAGTG GGGCCGCCCG CTGCAGTATC 100

ATTCAGTCAT TCACACCTCG CGCCATTGGC AAGATTGTTT TGCACCTTCC 150

TTACAGCAAC TTCGACAG 168

( 2 ) INFORMATION FOR SEQ ID NO:25:

( i ) SEQUENCE CHARACTERISTICS:
( A ) LENGTH: 216 base pairs
( B ) TYPE: Nucleic acid
( C ) STRANDEDNESS: Double stranded
( D ) TOPOLOGY: Linear ( i i ) MOLECULE TYPE:
( A ) DESCRIPTION: Genomic DNA ( v i ) ORIGINAL SOURCE:
( A ) ORGANISM: Clavibacter michiganensis ssp. sepedonicus (Cms)
( B ) STRAIN: Cs3

(vii) IMMEDIATE SOURCE:
 (A) LIBRARY: Genomic
 (B) CLONE: Cms 162

(ix) FEATURE:
 (A) NAME/KEY: EcoRI adaptor sequence
 (B) LOCATION: Underlined
 (C) IDENTIFICATION METHOD: Similarity to known sequence (xi) SEQUENCE DESCRIPTION: SEQ ID NO:25:

| | | | | | |
|---|---|---|---|---|---|
| TGCCAGCAGC | AAGTTAAGCA | GCAAGCCCTG | AGCAAGCACC | TCAGGGTGGA | 50 |
| GGACCACTCG | ATTCGTAGTG | TGCAAGCTGT | CGGCTGTCTG | ACGTATTGCT | 100 |
| GCCTGCAATC | TCAAAGCTTG | CTACGGGCAA | GCAAATGCCT | ATTCGGGTCG | 150 |
| GAGCGGTGGG | GAGTCGGTTA | CCGGGCGAC | AGCAACGGCG | ACAGCAACGG | 200 |
| CGACAGCAAC | GGAATT | | | | 216 |

(2) INFORMATION FOR SEQ ID NO:26:

(i) SEQUENCE CHARACTERISTICS:
  (A) LENGTH: 110 base pairs
  (B) TYPE: Nucleic acid
  (C) STRANDEDNESS: Double stranded
  (D) TOPOLOGY: Linear (ii) MOLECULE TYPE:
  (A) DESCRIPTION: Genomic DNA (vi) ORIGINAL SOURCE:
  (A) ORGANISM: Clavibacter michiganensis ssp. sepedonicus (Cms)
  (B) STRAIN: Cs3

(vii) IMMEDIATE SOURCE:
  (A) LIBRARY: Genomic
  (B) CLONE: Cms 163

(xi) SEQUENCE DESCRIPTION: SEQ ID NO:26:

| | | | | | |
|---|---|---|---|---|---|
| CGGGAGGCAG | CAGTGGGGAA | TATTGCACAA | TGGGCGAAAG | CCTGATGCAG | 50 |
| CAACGCCGCG | TGAGGGATGA | CGGCCTTCGG | GTTGTAAACC | TCTTTTAGTA | 100 |
| GGGAAGAAGC | | | | | 110 |

(2) INFORMATION FOR SEQ ID NO:27:

(i) SEQUENCE CHARACTERISTICS:
  (A) LENGTH: 21 nucleotides
  (B) TYPE: Nucleic acid
  (C) STRANDEDNESS: Single stranded
  (D) TOPOLOGY: Linear (ii) MOLECULE TYPE:
  (A) DESCRIPTION: Other nucleic acid (oligonucleotide)

(vi) ORIGINAL SOURCE:
  (A) ORGANISM: Clavibacter michiganensis ssp. sepedonicus (Cms)
  (B) STRAIN: Cs3

(vii) IMMEDIATE SOURCE:
  (A) LIBRARY: Genomic
  (B) CLONE: Cms 163 (Oligonucleotide chemically synthesized to correspond to nucleotides 4-24 of SEQ ID. NO:26)

(xi) SEQUENCE DESCRIPTION: SEQ ID NO:27:

GAGGCAGCAG TGGGAATAT T     21

(2) INFORMATION FOR SEQ ID NO:28:

-continued

```
    ( i ) SEQUENCE CHARACTERISTICS:
            ( A ) LENGTH: 25 nucleotides
            ( B ) TYPE: Nucleic acid
            ( C ) STRANDEDNESS: Single stranded
            ( D ) TOPOLOGY: Linear ( i i ) MOLECULE TYPE:
            ( A ) DESCRIPTION: Other nucleic acid
                    (oligonucleotide)

( v i ) ORIGINAL SOURCE:
            ( A ) ORGANISM: Clavibacter michiganensis ssp.
                    sepedonicus (Cms)
            ( B ) STRAIN: Cs3

( v i i ) IMMEDIATE S

4. An isolated nucleic acid according to claim 3 further comprising a detectable label.

5. An isolated nucleic acid according to claim 4 wherein the label is nonradioactive.

6. A recombinant vector comprising a nucleic acid molecule according to claim 1.

7. A transformed host cell comprising a nucleic acid according to claim 6.

8. A method for detecting the presence of a *Clavibacter michiganensis* ssp. sepedonicus cell in a biological sample comprising the cell, the method comprising the steps of:
   providing the biological sample;
   contacting the biological sample with an isolated nucleic acid to according to claim 3 under conditions conducive to hybridization of the isolated nucleic acid to a complementary DNA molecule, thereby forming a hybrid nucleic acid; and
   detecting the hybrid nucleic acid, wherein detection of the hybrid nucleic acid is indicative of the presence of the cell in the biological sample.

9. A method according to claim 8 wherein the isolated nucleic acid further comprises a detectable label and the step of detecting comprises detecting the presence of the label.

10. A method for detecting the presence of a *Clavibacter michiganensis* ssp. sepedonicus cell in a biological sample comprising the cell, the method comprising the steps of:
    providing the biological sample;
    contacting the biological sample with a pair of primers, each primer comprising an isolated nucleic acid sequence according to claim 4;
    performing a DNA amplification reaction, thereby producing an amplification product; and
    detecting the amplification product, wherein detection of the amplification product is indicative of the presence of the *Clavibacter michiganensis* ssp. sepedonicus cell in the biological sample.

11. A method according to claim 10 wherein the DNA amplification reaction is the polymerase chain reaction.

12. A method according to claim 10 wherein at least one of the primers further comprises a detectable label.

13. A method according to claim 12 wherein the label is nonradioactive.

14. A method of isolating a DNA fragment that is unique to *Clavibacter michiganensis* ssp. sepedonicus, the method comprising the steps of:
    providing *Clavibacter michiganensis* ssp. sepedonicus tester DNA fragments;
    providing driver DNA comprising DNA from a bacterial species related to *Clavibacter michiganensis* ssp. sepedonicus;
    hybridizing the tester DNA fragments to the driver DNA, thereby producing non-hybridizing tester DNA fragments; and
    isolating a non-hybridizing tester DNA fragment that (i) hybridizes under stringent hybridization conditions to DNA from *Clavibacter michiganensis* ssp. sepedonicus strains CS3 and P45, (ii) does not hybridize under stringent hybridization conditions to DNA from *Clavibacter michiganensis* ssp. insidiosus, *Clavibacter michiganensis* ssp. rathayi, *Curtobacterium flaccumfaciens* ssp. oortii, *Rhodococcus fascians*, and *Clavibacter michiganensis* ssp. michiganensis, and (iii) is non-ribosomal, thereby isolating a DNA fragment that is unique to *Clavibacter michiganensis* ssp. sepedonicus.

15. A DNA fragment unique to *Clavibacter michiganensis* ssp. sepedonicus that is produced by the method according to claim 14.

16. An isolated nucleic acid according to claim 1 wherein the non-ribosomal sequence does not hybridize under stringent hybridization conditions to DNA from *Pseudomonas putida*, *Pseudomonas fluorescens*, *Enterobacter cloacae*, *Agrobacterium tumefaciens*, *Erwinia carotovora*, *Alcaligenes xylosoxidans* ssp. denitrificans, *Micrococcus roseus*, and strains B, B2, and C2 that cross-react with antibodies prepared against *Clavibacter michiganensis* ssp. sepedonicus.

17. An isolated nucleic acid according to claim 1, wherein the non-ribosomal sequence flanks a sequence selected from the group consisting of SEQ ID NO:1, SEQ ID NO:2, SEQ ID NO:3, SEQ ID NO:6, SEQ ID NO:7, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:24, and SEQ ID NO:25, and wherein the non-ribosomal sequence is produced by a method comprising the steps of:
    providing a probe comprising a nucleic acid having 100% similarity or complementarity to a sequence selected from the group consisting of SEQ ID NO:1, SEQ ID NO:2, SEQ ID NO:3, SEQ ID NO:6, SEQ ID NO:7, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:24, and SEQ ID NO:25;
    providing a *Clavibacter michiganensis* ssp. sepedonicus genomic library;
    contacting the genomic library with the probe under conditions conducive to specific hybridization of the non-ribosomal sequence to a complementary sequence;
    isolating from the library a genomic clone that hybridizes to the probe;
    determining whether the fragment of the genomic clone hybridizes under stringent hybridization conditions to DNA from *Clavibacter michiganensis* ssp. sepedonicus strains CS3 and P45 and does not hybridize under stringent hybridization conditions to *Clavibacter michiganensis* ssp. insidiosus, *Clavibacter michiganensis* ssp. rathayi, *Curtobacterium flaccumfaciens* ssp. oortii, *Rhodococcus fascians*, and *Clavibacter michiganensis* ssp. michiganensis; and
    determining whether the fragment of the genomic clone is ribosomal.

18. An isolated nucleic acid according to claim 1 wherein the non-ribosomal sequence flanks a sequence selected from the group consisting of SEQ ID NO:1, SEQ ID NO:2, SEQ ID NO:3, SEQ ID NO:6, SEQ ID NO:7, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:24, and SEQ ID NO:25, and wherein the non-ribosomal sequence is produced by a method comprising the steps of:
    providing *Clavibacter michiganensis* ssp. sepedonicus genomic DNA;
    contacting the genomic DNA with an amplification primer comprising a nucleic acid having 100% similarity or complementarity to a sequence selected from the group consisting of SEQ ID NO:1, SEQ ID NO:2, SEQ ID NO:3, SEQ ID NO:6, SEQ ID NO:7, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:24, and SEQ ID NO:25;

performing an amplification reaction, thereby producing an amplified genomic DNA sequence;

hybridizing the amplified genomic DNA sequence under stringent hybridization conditions to DNA from *Clavibacter michiganensis* ssp. sepedonicus strains CS3 and P45, *Clavibacter michiganensis* ssp. insidiosus, *Clavibacter michiganensis* ssp. rathayi, *Curtobacterium flaccumfaciens* ssp. oortii, *Rhodococcus fascians*, and *Clavibacter michiganensis* ssp. michiganensis; and determining whether the amplified genomic DNA sequence is ribosomal.

19. The isolated nucleic acid according to claim 3 wherein the sequence comprises at least 19 contiguous nucleotides having 100% similarity or complementarity to a sequence selected from the group consisting of SEQ ID NO:1, SEQ ID NO:2, SEQ ID NO:3, SEQ ID NO:6, SEQ ID NO:7, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:24, and SEQ ID NO:25.

20. The isolated nucleic acid according to claim 19 wherein the sequence comprises at least 22 contiguous nucleotides having 100% similarity or complementarity to a sequence selected from the group consisting of SEQ ID NO:1, SEQ ID NO:2, SEQ ID NO:3, SEQ ID NO:6, SEQ ID NO:7, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:24, and SEQ ID NO:25.

21. The isolated nucleic acid according to claim 20 wherein the sequence comprises at least 24 contiguous nucleotides having 100% similarity or complementarity to a sequence selected from the group consisting of SEQ ID NO:1, SEQ ID NO:2, SEQ ID NO:3, SEQ ID NO:6, SEQ ID NO:7, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:24, and SEQ ID NO:25.

22. The isolated nucleic acid according to claim 21 wherein the sequence comprises a full-length sequence selected from the group consisting of SEQ ID NO:1, SEQ ID NO:2, SEQ ID NO:3, SEQ ID NO:6, SEQ ID NO:7, SEQ ID NO:11, SEQ ID NO:12, SEQ ID NO:15, SEQ ID NO:16, SEQ ID NO:17, SEQ ID NO:18, SEQ ID NO:19, SEQ ID NO:20, SEQ ID NO:24, and SEQ ID NO:25.

23. A method for detecting the presence of a *Clavibacter michiganensis* ssp. sepedonicus cell in a biological sample comprising the cell, the method comprising the steps of:

providing the biological sample;

contacting the biological sample with an amplification primer comprising an isolated nucleic acid according to claim 3;

performing a DNA amplification reaction, thereby producing an amplification product; and detecting the amplification product, wherein detection of the amplification product is indicative of the presence of the *Clavibacter michiganensis* ssp. sepedonicus cell in the biological sample.

* * * * *

UNITED STATES PATENT AND TRADEMARK OFFICE
CERTIFICATE OF CORRECTION

PATENT NO. : 5,710,002
DATED : January 20, 1998
INVENTOR(S) : Dallice I. Mills

It is certified that error appears in the above-identified patent and that said Letters Patent is hereby corrected as shown below:

Column 43,
Line 31, "sequence according to claim 4;" should read -- sequence according to claim 3; --.

Signed and Sealed this

Thirtieth Day of March, 2004

JON W. DUDAS
*Acting Director of the United States Patent and Trademark Office*